(12) United States Patent
Ohlin

(10) Patent No.: US 9,956,138 B2
(45) Date of Patent: May 1, 2018

(54) PROTECTIVE CAP

(75) Inventor: Gunnar Ohlin, Västra Frölunda (SE)

(73) Assignee: Carmel Pharma AB, Gothenburg (SE)

( * ) Notice: Subject to any disclaimer, the term of this patent is extended or adjusted under 35 U.S.C. 154(b) by 212 days.

(21) Appl. No.: 14/401,752

(22) PCT Filed: May 21, 2012

(86) PCT No.: PCT/SE2012/050546
§ 371 (c)(1),
(2), (4) Date: Sep. 23, 2015

(87) PCT Pub. No.: WO2013/176587
PCT Pub. Date: Nov. 28, 2013

(65) Prior Publication Data
US 2016/0038373 A1 Feb. 11, 2016

(51) Int. Cl.
*A61J 1/00* (2006.01)
*A61J 1/14* (2006.01)
*A61M 39/04* (2006.01)
*B65D 51/00* (2006.01)
*A61J 1/05* (2006.01)

(52) U.S. Cl.
CPC ........... *A61J 1/1406* (2013.01); *A61J 1/1412* (2013.01); *A61J 1/1425* (2015.05); *A61M 39/04* (2013.01); *B65D 51/002* (2013.01); *A61J 1/05* (2013.01)

(58) Field of Classification Search
CPC ...... A61J 1/1406; A61J 1/1425; A61J 1/1412; A61J 1/05; B65D 51/002; A61M 39/04
USPC .................................. 215/247, 249; 604/415
See application file for complete search history.

(56) References Cited

U.S. PATENT DOCUMENTS

| 3,900,028 | A |   | 8/1975 | McPhee |   |
|---|---|---|---|---|---|
| 4,564,054 | A |   | 1/1986 | Gustaysson |   |
| 4,671,331 | A |   | 6/1987 | Pruden |   |
| 4,967,919 | A | * | 11/1990 | Earhart | A61B 5/15003 215/247 |
| 5,232,111 | A | * | 8/1993 | Burns | B01L 3/50825 215/247 |
| 5,361,921 | A | * | 11/1994 | Burns | B01L 3/50825 215/247 |
| 5,494,170 | A | * | 2/1996 | Burns | B01L 3/50825 215/247 |
| 2004/0118803 | A1 | * | 6/2004 | Claessens | B01L 3/50825 215/247 |
| 2004/0199139 | A1 |   | 10/2004 | Fowles et al. |   |

(Continued)

FOREIGN PATENT DOCUMENTS

CA 2872434 A1 3/2009
CN 1886295 A 12/2006

(Continued)

*Primary Examiner* — James N Smalley
(74) *Attorney, Agent, or Firm* — The Webb Law Firm

(57) ABSTRACT

A protective cap (1) for application on a medical device such as a medical vial (2) comprising a membrane holder (3) in which a resilient membrane (18) is mounted. The protective cap (1) is provided with connection means (10) for connecting the cap (1) to the medical device (2). The resilient membrane (18) comprises a piercing portion (20) and a sealing portion (22) and is mechanically and/or adhesively held in the protective cap (1) and is arranged to be brought into sealing contact with a receiving portion of the medical device (2) when the protective cap (1) is applied on the medical device (2).

16 Claims, 3 Drawing Sheets

(56) References Cited

U.S. PATENT DOCUMENTS

| | | | |
|---|---|---|---|
| 2009/0054865 A1* | 2/2009 | Brandenburger | B65D 51/002 604/415 |
| 2010/0218846 A1 | 9/2010 | Kriheli | |
| 2013/0184672 A1 | 7/2013 | Nord et al. | |
| 2014/0000738 A1 | 1/2014 | Reynolds et al. | |
| 2014/0020792 A1 | 1/2014 | Kraus et al. | |

FOREIGN PATENT DOCUMENTS

| | | |
|---|---|---|
| JP | 48111542 | 1/1973 |
| JP | 2008222270 A | 9/2008 |
| WO | 2004004806 A1 | 1/2004 |
| WO | 2008129550 A2 | 10/2008 |
| WO | 2008136720 A1 | 11/2008 |
| WO | 2010127691 A1 | 11/2010 |
| WO | 2011060829 A1 | 5/2011 |
| WO | 2012119225 A1 | 9/2012 |

* cited by examiner

PROTECTIVE CAP

CROSS-REFERENCE TO RELATED APPLICATIONS

This application is the United States national phase of International Application No. PCT/SE2012/050546 filed May 21, 2012, the disclosure of which is hereby incorporated in its entirety by reference.

TECHNICAL FIELD

The invention relates to a protective cap for application on a medical device such as a medical vial, said protective cap comprising a membrane holder having a first end with an end wall, said end wall having an outer surface and an inner surface and a second end at a distance from said first end said second end being adapted to be placed over a receiving portion of said medical device and being provided with connection means for connecting said protective cap to said medical device.

BACKGROUND OF THE INVENTION

A major problem in relation to drug preparation, drug administration or other similar handling of pharmaceuticals is the risk of medical and pharmacological staff being exposed to drugs or solvents which may escape into ambient air. The problem is particularly serious when hazardous drugs such as cytotoxics, antiviral drugs, antibiotics and radiopharmaceuticals are concerned. Other hazards may arise when taking samples relating to virus infections or the like. For these reasons, systems for handling and administrating drugs and other medical substances under improved safety conditions have been developed.

U.S. Pat. No. 4,564,054 (Gustavsson) discloses a fluid transfer device for preventing air contamination when transferring a substance from a first vessel to a second vessel. The device is attached or connectible to the vessel and comprises a first member, in which a piercing member e.g. a needle, provided with a passage is enclosed. The first member has a sealing member e.g. a membrane, through which the needle can be passed. The device further comprises a second chamber, which is detachably connectable to the first member and which also has a sealing member, e.g. a membrane. When the first and second members are connected to each other, the two sealing members are located in a position with respect to each other so that they can be penetrated by the piercing member which is movable with respect to the sealing member.

The sealing members are resilient liquid and gas-proof barriers having the ability of sealing tightly after penetration and retraction of the piercing member to prevent leakage of liquid as well as gas components.

Another example of a device using a barrier member is found in U.S. Pat. No. 3,900,028 in which is disclosed an injection site arrangement for a vessel having a first cylindrical member interposed in a second cylindrical member and a barrier member arranged between the first and second members. During manufacturing of the injection site arrangement, the second member is telescopically inserted into an opening at a lower end of the first member. The barrier member is tightly compressed in the longitudinal direction of the first and second members. The first cylindrical member is thereafter fixed to the second cylindrical member by means of a rib on the first cylindrical member and a corresponding groove an the second cylindrical member. The rib of the first cylindrical member is formed by deformation of the lower edge of the first cylindrical member by subjecting it to heat and pressure during the manufacturing of the injection site arrangement.

The barrier members used in the protective systems are usually made from a resiliently compressible material such as a natural or synthetic rubber or a rubber like material. However, it has been found that medical devices such as those mentioned above have certain limitations.

Resilient barrier members are commonly made from a thermoplastic elastomeric polymer material (TPE) allowing the members to be affixed in a protective injecting device by ultrasonic welding. The ultrasonic welding procedure is temperature dependent and has to be carefully controlled as the manufacturing tolerances are small. Consequently, production of the prior art protective injection devices is complicated and costly. The barrier members are mounted in the protective injecting devices with a predetermined amount of tensioning compression. The amount of tension applied to the barrier member is critical. If the barrier member is too highly tensioned, it may result in the piercing member punching out a piece of the membrane when the membrane is penetrated. On the other hand, if the tensioning of the membrane is too low, the injection site will not close completely after removal of a piercing member. Accordingly, mounting of the resilient barrier members requires a carefully controlled process.

A further problem is that resilient barrier members are subject to aging and may loose some of the production induced tension over time.

It has been suggested in WO 2010/127691 A1 to apply the resilient barrier member between two parts of a protective injection device. A first part of the protective injection device in WO 2010/127691 A1 is a connecting part for connecting the device with a medical appliance such as a vial and the second part is a tensioning part that can be locked in engagement with the first part with the resilient barrier member clamped between the two parts. In the interlocked position of the parts, the resilient barrier member is subjected to a working tensioning force.

The protective injection device in WO 2010/127691 A1 has been found to work very well in diminishing the problems with aging and production tolerances. An objective with the present invention is to offer a further improved protective injection device.

SUMMARY OF THE INVENTION

In accordance with the invention is offered a protective cap for application on a medical device such as a medical vial. The protective cap comprises a membrane holder having a first end with an end wall, the end wall having an outer surface and an inner surface and a second end with an end opening at a distance from the first end, the second end being adapted to be placed over a receiving portion of the medical device and being provided with connection means for connecting the protective cap to the medical device, the end wall of the membrane holder having an opening, the opening having a peripheral edge, wherein a resilient membrane is arranged to cover the opening, the resilient membrane comprising a piercing portion and a sealing portion, the membrane holder comprising attachment means for attaching the resilient membrane to the membrane holder the attachment means being an adhesive attachment means or a mechanical attachment means or a combination of an adhesive attachment means and a mechanical attachment means, the resilient membrane being attached in the membrane holder with the piercing portion of the resilient membrane exposed through the opening in the end wall of the membrane holder and with the sealing portion the resilient membrane arranged to be brought into sealing contact with the receiving portion of the medical device when the protective cap is applied on the medical device.

The barrier membrane of the invention may be made from medical grade elastomeric polymer materials as known in the art. Such materials include silicone elastomers natural elastomers and thermoplastic elastomeric polymer materials (TPC). Thermoplastic elastomers include Styrene Block Copolymers (TPS), Thermoplastic Polyolefins (TPO), Thermoplastic polyurethanes (TPU), copolyesters and polyether block amides.

By "elastomer" as used herein is implied a macromolecular material which returns rapidly to its initial dimension and shape after substantial deformation by a weak stress and release of the stress. The definition applies under room temperature test conditions and is found in ISO 472:1999 "Plastics Vocabulary".

The resilient membrane of the protective cap is arranged to be pressed into contact with and to form a gasketing, seal against a receiving surface on the medical device. The medical device may be a vial or other type of vessel or container for a liquid substance such as a medicament, a fluid sample or similar. A vial containing a medical liquid is commonly sealed with a cap and a rubber stopper that may be pierced by a needle e.g. for removal of a quantity of the liquid from the vial. "Stoppers" or closures for receptacles are defined by International Standards such as ISO 8362-5 and ISO 8536-2:20110. Upon application of the protective cap of the invention over the sealing cap on the vial and after connecting the protective cap with the vial, the resilient membrane is brought to abut the rubber stopper on the vial and to be sealingly pressed against the rubber stopper. In this manner, a double safety barrier is created at the mouth of the vial. The double barrier may be penetrated by a piercing member and will resiliently close after the piercing member has been retracted from the vial, thus preventing escape of the contents in the vial through the penetration site. At the same time, the gasketing seal between the resilient membrane on the protective cap and the rubber membrane of the vial prohibits sideways leakage of substance which may be released upon retraction of the piercing member.

The resilient membrane may be held in the membrane holder of the protective cap solely by mechanical forces. Accordingly, the welding step may be omitted, allowing assembly of the protective cap to be made accurately and efficiently at increased speed, without unduly increasing, the number of rejected caps in the process.

The resilient membrane in the protective cap of the invention need not be subjected to a working tension until the protective cap is applied on a receiving part of a medical device.

By the term "working tension" as used herein is meant that the resilient membrane is tensioned to a sufficient degree to obtain satisfactory closing of a penetration site after removal of a piercing member but not to a degree where the piercing member will cause permanent damage to the membrane. When held mechanically in the membrane holder, the resilient membrane may be under slight tension in order to keep the membrane from falling out of the membrane holder. However, such "attachment forces" may be very low and are preferably below the forces required to reach the working tension of the membrane. In this manner, the problems with aging and relaxation of the membrane during transport and storage which were found in prior art protective barrier caps may be avoided or at least greatly reduced.

Accordingly, the working, life of the resilient membrane may be increased as the membrane can be transported and stored in a practically non-tensioned state. The final tensioning in order to achieve a working tension in the resilient, membrane may be accomplished when the protective cap is connected to a medical device as will be further described herein.

The end wall and the opening in the end wall may have circular shape with the opening being centrally arranged in the end wall. A circular protective cap would be the most usual shape as the connective parts of medical equipment such as tubes and vials are generally tubular. However, other shapes such as square shapes, oval shapes etc, are contemplated to suit differently shaped medical devices.

The sealing portion of the resilient membrane may peripherally surround the piercing portion of the resilient membrane. This means that the sealing portion of the resilient membrane may extend laterally out from the piercing portion in a plane parallel to the plane of the membrane holder end wall.

The sealing portion may form part of the piercing portion of the resilient membrane in an axial direction perpendicular to the end wall of the membrane holder. In order to be able to form a seal against a receiving surface on a medical device, the sealing portion of the resilient membrane extends in the axial direction at least to the inner surface of the end wall of the membrane holder. Preferably, the sealing portion extends in the axial direction somewhat past the inner surface of the end wall so that a portion of the compressible resilient membrane protrudes from the inner surface of the membrane holder end wall.

The mechanical holding means may comprise a holding flange surrounding the peripheral edge of the opening in the membrane holder and being arranged at an angle at the outer surface of the end wall of the membrane holder. Accordingly, the holding flange is arranged such that it protrudes from the outer surface of the membrane holder end wall and is inclined towards the opening in the end wall. The resilient membrane is placed with the piercing portion arranged inside the flange such that the size and shape of the piercing portion are defined by the edge of the holding flange. A mechanical holding means of this type may be preferred over the two-part mechanical holders disclosed in WO 2010/127691 A1 as they have a simple, yet reliable construction and may be produced with cost efficiency.

The holding flange serves to keep the resilient membrane from falling out through the opening in the end wall in a direction towards the outer surface of the end wall. In order to keep the membrane in place and restrict its movement in a direction towards the inner surface of the end wall, the membrane may be applied with a slight lateral compression from the sides of the opening in the end wall. Attachment between the membrane and the membrane holder may be further improved by increasing friction and/or mechanical engagement between the membrane and the membrane holder at the opening in the end wall. Such attachment enhancing means may be threads, ridges, spikes or other irregularities in the walls of the opening. Enhanced friction may also be achieved by application of a coating, such as a rubber coating or particle coating on the walls of the opening.

The protective cap may be formed by injection molding and the different properties in different parts of the cap may be obtained using multicomponent injection molding techniques. By the term "multicomponent injection molding" as used herein is meant injection molding of two or more components.

The sealing portion of the membrane may be arranged to extend laterally past the peripheral edge of the opening on the inner surface of the end wall of the membrane holder in order to provide a large sealing surface that may be brought into sealing contact with a corresponding receiving, surface on a medical device.

In an alternative embodiment, the membrane holder may have a construction as disclosed in WO 2010/127691 A1 comprising an inner part and an outer part with the membrane being mechanically held between the inner part and the outer part of the membrane holder The connecting means for connecting the protective cap to a medical device such as a vial or other medical container having a transfer opening, may be of a kind that is arranged to engage with a corresponding connecting means on the medical device. Such connecting means may be snap-lock connectors where a rim or groove on the protective cap is designed to engage with a corresponding rim or groove on the medical device. A non-limiting example of a suitable snap-lock connecting means is a rim or hook arranged on the protective cap that will engage with a rim formed by an edge portion of a medical flask or vial. Other suitable connecting means may be the one-way threaded connectors disclosed in WO 2010/127691 A1.

Accordingly, the connecting means on the membrane holder may comprise an inner rim arranged at the edge of the end opening of the membrane holder. The inner rim may have inwardly slanted guiding edges for guiding the protective cap onto a receiving medical device such as the cap of a medical bottle or vial.

The protective cap may be provided with means for connecting an injection device to the protective cap at the outer surface of the membrane holder end wall. Such connecting means are well known in the art and include bayonet fittings, snap fittings and threaded fittings. Some suitable connecting means are disclosed in WO 2004/004806 A1.

BRIEF DESCRIPTION OF THE DRAWINGS

The invention will be described in greater detail with reference to the appended drawings in which.

DETAILED DESCRIPTION OF PREFERRED EMBODIMENTS

Figure 1:
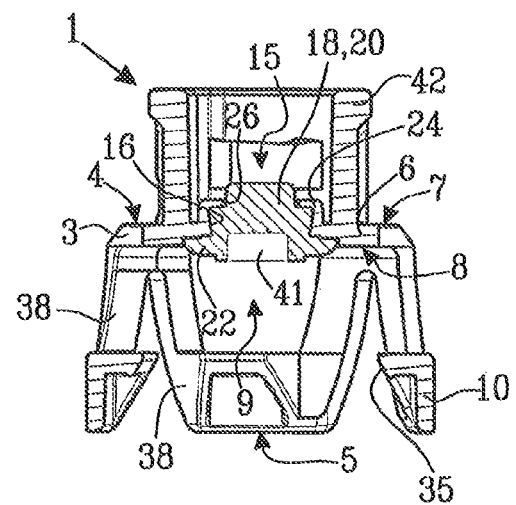
FIG. 1 shows a cross-sectional view of a protective cap according to the invention in the process of being applied to a vial.
Figure 1:
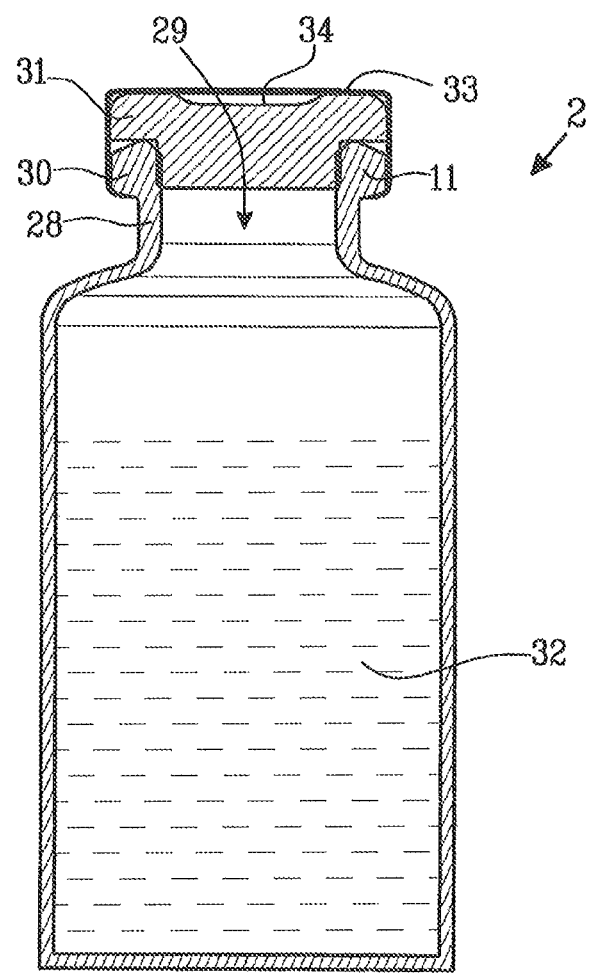

FIG. 1 shows a protective cap 1 and a medical device in the form of a vial 2. The protective cap 1 comprises a membrane holder 3 having a first end 4 with an end wall 6. The end wall 6 has an outer surface 7 and an inner surface 8. A second end 5 is arranged at a distance from the first end 4 and is provided with an end opening 9. The second end 5 is arranged to be connected to the vial 2 and is provided with first connection means 10 placed at the periphery of the end opening 9 and intended to engage with cooperating second connection means 11 on the vial 2.

The end wall 6 of the membrane holder 3 is provided with a central piercing opening 15. The piercing opening 15 has a peripheral edge 16. A resilient membrane 18 is arranged to cover the piercing opening 15. The resilient membrane 18 has a piercing portion 20 and a sealing portion 22 peripherally surrounding the piercing portion 20.

The resilient membrane 18 is attached to the membrane holder 3 by mechanical holding means in the form of a holding flange 24 surrounding the peripheral edge 16 of the piercing opening 15 in the membrane holder 3. The holding flange 24 is shown to be arranged at an angle at the outer surface 7 of the end wall 6 of the membrane holder 3 and protrudes from the outer surface 7 of the membrane holder end wall 6. The holding flange 24 is inclined towards the centre of the piercing opening 15, causing the circumference of the piercing opening 15 to be smaller at the outer edge 26 of the holding flange 24 than in the plane of the end wall 6 of the membrane holder 3. The resilient membrane 18 is placed with the piercing portion 20 arranged inside the holding flange 24. This means that the size and shape of the piercing portion 20 as seen from the outer surface 7 of the membrane holder 3 are defined by the outer edge 26 of the holding flange 24.

The holding, flange 24 serves to keep the resilient membrane 18 from falling out through the piercing opening 15 in a direction towards the outer surface 7 of the end wall 6. In order to keep the membrane in place and restrict its movement in a direction towards the inner surface 8 of the end wall 6, the membrane 18 may be applied with a slight lateral tensioning keeping it pressed against the edge 16 of the piercing opening 15 and against the inner surface of the holding flange 24. The edge 16 of the piercing opening 15 and the inner surface of the holding flange 24 may be provided with threads, ridges, spikes or other physical elements to enhance friction and/or mechanical engagement between the material in the membrane holder 3 and the resilient membrane 18. Enhanced friction and improved fixation of the membrane may also be achieved by means of a coating, such as a rubber coating or particle coating on the edges of the opening and on the inside of the holding flange 24. Adhesives may also be used to improve fixation of the resilient membrane in the membrane holder. A further possibility is to form the membrane holder and the membrane in a multi-component injection molding process.

The sealing portion 22 of the resilient membrane 18 extends laterally past the peripheral edge 16 of the opening on the inner surface 8 of the end wall of the membrane holder 3.

Figure 2:
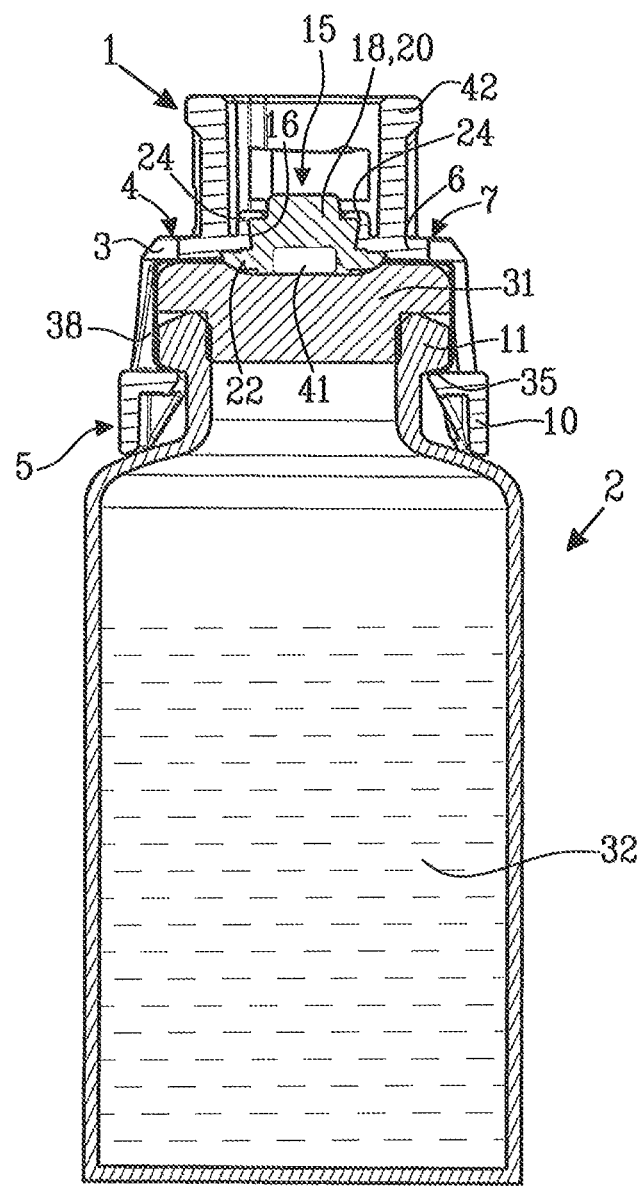
FIG. 2 shows a cross-sectional view of the protective cap in FIG. 1 after application to the vial.
Figure 3:
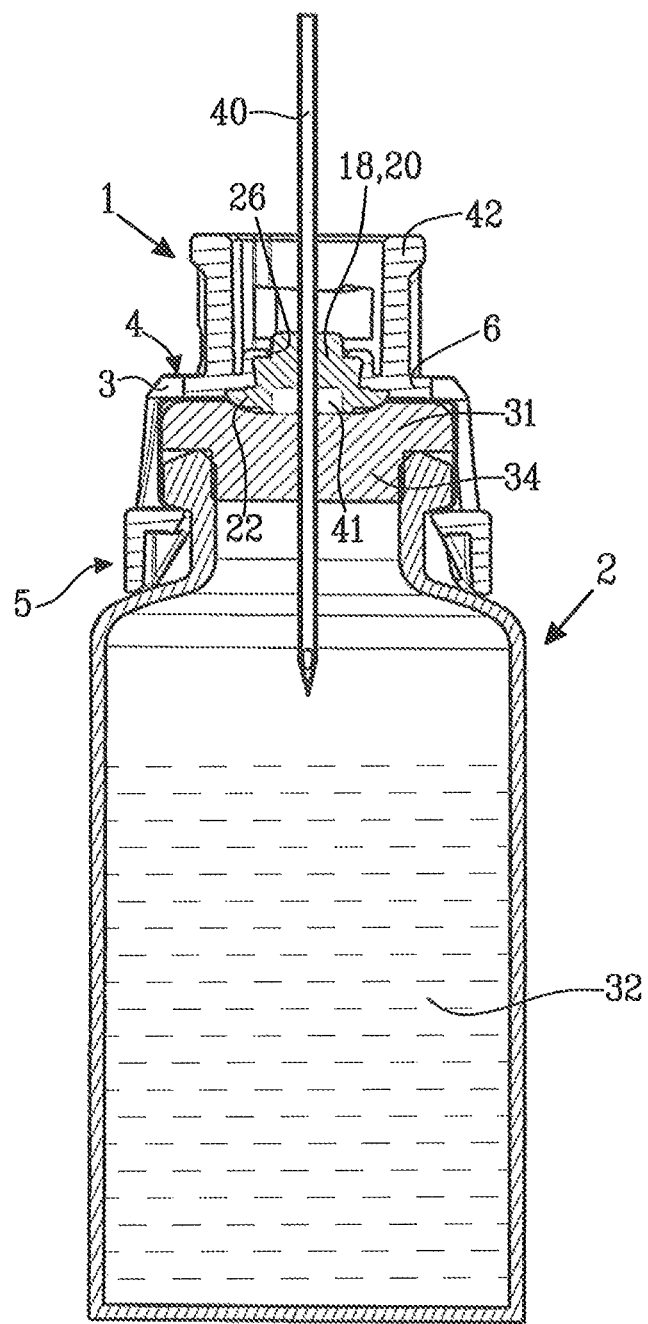
FIG. 3 shows a cross-sectional view of the protective cap and vial in FIGS. 1 and 2 with a piercing member inserted in the vial through the protective cap.

The protective cap 1 is configured to fit over the end of a medical device illustrated by the vial 2 shown in FIGS. 1-3. The vial 2 is only intended to be an example of a medical device that can be provided with additional protection against contamination by bacteria or other foreign matter from the environment or from unwanted escape of liquid from inside the of the medical device. Only the upper part of the vial 2 is shown in FIGS. 1-3 as this is the receiving part of the vial 2 that will engage with the protective cap.

The vial 2 is a small glass bottle with a bottle neck 28 and a bottle opening 29. A rim 30 extends around the bottle opening 29 and serves as the second connection means 11 that will cooperate with the first connection means 10 on the protective cap 1 when the protective cap 1 is pushed down over the bottle neck 28. A sealing member 31 is inserted into the bottle neck 28 through the bottle opening 29 in order to keep the fluid 32 that is contained in the vial 2 from escaping out through the bottle opening 29. The sealing member 31 is commonly a rubber stopper which may be penetrated by a piercing member such as an injection needle. The interface between the sealing member 31 and the rim 30 at the bottle opening 29 is further sealed by means of a protective foil 33 extending around the bottle opening 29 with a first end portion on the exposed surface of the sealing member 31 and a second end portion beneath the rim 30 around the bottle opening 29. Accordingly, the protective foil 33 is wrapped around an edge portion of the upper part of the vial 2, leaving only a circular piercing area 34 exposed at the centre of the sealing member 31.

The first connection means 10 is shown in FIGS. 1-3 to be hook elements 35 arranged at the end opening 9 of the membrane holder 3. The hook elements 35 are configured to fit under the rim 30 around the bottle opening 29 in the vial 2 to keep the protective cap 1 locked in position over the bottle opening 29 with the piercing portion 20 of the resilient membrane 18 in the protective cap 1 aligned with the piercing area 34 on the sealing member and with the sealing portion 22 of the resilient membrane 18 pressed against the exposed surface of the sealing member 31 in the bottle opening 29. In order to facilitate expansion of the protective cap, the side wall between the first and second ends 4,5 of the membrane holder 3 is divided into flexible tongues 38. The flexible tongues may be two or more, such as four flexible tongues in order to facilitate expansion of the membrane holder when applying it to a vial or other medical container. The hook elements 35 are arranged at the free ends of the flexible tongues 38. Alternatively, the side wall of the membrane holder 3 may be provided with slits extending, in the axial direction of the membrane holder 3. The material in the membrane holder 3 should be of a kind that is elastically flexible, i.e. elastically bendable, so that the end opening 9 in the protective cap 1 can be expanded sufficiently to allow the hook elements 35 on the protective cap 1 to pass down below the rim 30 around the bottle opening and to spring back into locking engagement with the bottle neck 28, fitting below the rim 30 around the bottle opening 29.

With reference to ISO 472:1999 "Plastics—Vocabulary" a "flexible material" as used herein is implied a material that can be folded or twisted or bent by hand or a material that may be flexed and/or bent repeatedly without rupture or development of visible defects.

In order to facilitate application of the protective cap 1 on the vial 2, the edges of the inner rim 35 on the protective cap 1 may be slanted as shown in the figures. The slanted edges serve as guide means and induce expansion of the end opening 9 in the protective cap 1 as the protective cap 1 is pressed down on the vial.

When the protective cap 1 is applied to the vial 2 as shown in FIG. 2, the resilient membrane 18 is subjected to a working tension by the sealing portion 22 of the membrane 18 being compressed between the inner surface 8 of the membrane holder 3 and the exposed surface of the sealing member 31 in the bottle opening 29. The resilient membrane 18 is maintained at a working tension as long as the protective cap is connected to the vial 2.

A particular advantage with the protective cap of the invention is that the membrane is brought into direct and sealing contact with a surface on the medical device to which the protective cap is applied. As shown in FIG. 2, the sealing part 22 of the resilient membrane 18 is directly contacting a portion of the piercing area 34 on the sealing member 31 in the bottle opening 29, The elastomeric polymer material in the resilient membrane 18 and in the sealing member 31 on the vial 2 together form an excellent barrier to lateral fluid leakage out between the resilient membrane 18 and the sealing member 31. The seal between the resilient membrane 18 and the sealing member 31 on the vial 2 prohibits fluid that may be emitted from the piercing member 40 as the piercing member is being withdrawn from the vial 2 from escaping out between the resilient membrane 18 and the sealing member 31 on the vial 2. As is shown in FIGS. 1-3, the resilient membrane 18 has a cavity 41 which is located between the resilient membrane 18 and the sealing member 31 on the vial 2 when the protective cap 1 is mounted on the vial 2. The cavity 41 is arranged to capture any fluid that is emitted from the piercing member 40 when it is withdrawn from the vial 2.

FIG. 3 illustrates the appearance of the protective cap 1 when mounted on the vial 2 and while being pierced by a piercing member 40. The piercing member 40 penetrates both the piercing portion 20 of the resilient membrane 18 and the piercing area 34 on the vial sealing member 31 and reaches down into the fluid contained in the vial 2. When the desired amount of fluid has been removed from the vial 2 through the piercing member 40, the piercing member is withdrawn and the piercing site will close due to the resiliency in the membrane material and the sealing member material. The working tension applied to the resilient membrane aids in attaining a satisfactory closing of the piercing site.

A receiving part of a coupling arrangement 42 in the form of a bayonet fitting intended for attaching a medical device, such as a pressure equalizing device or an injection device at the outer surface 7 of the membrane holder 3 is shown in FIGS. 1-3. The coupling arrangement 42 serves to form a stable connection between the connecting means and the medical device. The coupling arrangement 42 may also serve to protect and guide a piercing member during piercing of the protective seal on a medical container or other medical device when fluids are to be transferred from the medical device or into the medical device through a protective membrane as disclosed herein. The coupling arrangement may be a PhaSeal® bayonet fitting or other type of coupling element for coupling a medical device such as an injection device to the outer end of the protective cap. The connecting means may be any type of bayonet fitting, snap fitting, threaded fitting, leer lock, etc., as known in the art.

The coupling arrangement 42 may be formed integrally with the protective cap 1, from the same or different materials. Thermoplastic materials such as polyethylene or polypropylene; acrylonitrile butadiene styrene (ABS), polycarbonate, polyester or any other suitable materials may be used. When using injection molding techniques to form the protective caps of the invention, the process may be a monocomponent or multicomponent injection molding process allowing different parts of the protective cap to be formed integrally from materials having different properties, such as different extensibility, different flexibility, etc.

The protective cap of the invention is intended for use as an adapter on a medical device such as a medical vial or flask for transfer of fluid into and out of the device. The protective cap comprises two main components made from different materials. A first material provides the protective cap with a general shape and structure and acts as a holder for the second material. The first material may be flexible so that the protective cap can be radially expanded when subjected to extension forces and so that the protective cap will elastically return to its non-expanded state when the extension forces are removed. The second material is generally softer than the first material and is resiliently compressible. The second material acts as a membrane or secondary barrier to the medical device. When the protective cap is applied to a medical device such as a vial being closed with a rubber stopper, the resilient second material contacts the rubber stopper of the vial and seals against leakage of fluid from the vial or contamination of the contents in the vial from the environment. The seal is particularly efficient as it involves contact between resiliently compressible members that conform to each other and form an extremely tight seal.

The protective cap of the invention is shaped and sized to fit the particular medical device which it is intended to be connected to.

The invention claimed is:

1. A protective cap having a longitudinal axis for application on a medical device having a sealing member, said protective cap comprising:
   a membrane holder having a first end with an end wall, said end wall having an outer surface and an inner surface and a second end with an end opening at a distance from said first end, said second end being adapted to be placed over a receiving portion of said medical device and being provided with a connection arrangement for connecting said protective cap to said medical device, said end wall of said membrane holder having a holding flange protruding in an axial direction from the outer surface of the end wall, the holding flange defining a piercing opening said piercing opening having a peripheral edge; and
   a resilient membrane arranged to cover said piercing opening, said resilient membrane comprising a piercing portion arranged inside said holding flange and a sealing portion defining a cavity,
   wherein said holding flange or said peripheral edge of said membrane holder comprises an attachment arrangement for attaching said resilient membrane to said holding flange or said peripheral edge of said membrane holder, said attachment arrangement being an adhesive attachment or a mechanical attachment or a combination of an adhesive attachment and a mechanical attachment, and
   wherein said resilient membrane is attached in said membrane holder with said piercing portion of said resilient membrane exposed through said piercing opening defined by said holding flange with an exterior edge of said cavity being positioned entirely radially inward from said peripheral edge of said piercing opening relative to said longitudinal axis and said sealing portion extending radially beyond said peripheral edge of said piercing opening and positioned adjacent to said inner surface of said end wall and extending from said inner surface in an axial direction toward said second end of said membrane holder, such that said sealing portion of said resilient membrane is arranged to be brought into sealing contact with said sealing member of said medical device when said protective cap is applied to said medical device.

2. The protective cap according to claim 1, wherein said end wall and said piercing opening in said end wall have a circular shape and wherein said piercing opening is centrally arranged in said end wall.

3. The protective cap according to claim 1, wherein said sealing portion of said resilient membrane peripherally surrounds said piercing portion of said resilient membrane.

4. The protective cap according to claim 1, wherein said sealing portion of said resilient membrane forms part of said piercing portion of said resilient membrane.

5. The protective cap according to claim 1, wherein said holding flange is arranged at an angle at said outer surface of said end wall of said membrane holder and is inclined towards said piercing opening in said end wall of said membrane holder.

6. The protective cap according to claim 1, wherein said sealing portion of said membrane extends past said peripheral edge of said piercing opening on said inner surface of said end wall of said membrane holder.

7. The protective cap according to claim 1, wherein said membrane holder comprises an inner part and an outer part, said membrane being mechanically held between said inner part and said outer part of said membrane holder.

8. The protective cap according to claim 1, wherein said connecting arrangement for connecting said protective cap to said medical device is arranged to engage with a corresponding connection on said medical device.

9. The protective cap according to claim 8, wherein said connecting arrangement on said membrane holder comprises a hook element arranged at said end opening of said membrane holder.

10. The protective cap according to claim 9, wherein said hook element has an inwardly slanted guiding edge.

11. The protective cap according to claim 1, wherein a coupling arrangement for connecting a medical device carrying a piercing member to said protective cap is arranged at said outer surface of said membrane holder end wall.

12. The protective cap according to claim 1, wherein said mechanical attachment comprises one or more of threads, ridges, and spikes on an inner surface of said holding flange for enhancing friction or mechanical engagement between said membrane holder and said resilient membrane.

13. The protective cap according to claim 1, wherein said adhesive attachment comprises an adhesive on an inner surface of said holding flange and/or on said inner surface of said end wall.

14. The protective cap according to claim 1, wherein said holding flange comprises a lip extending radially inward from the peripheral edge, the lip having an inner surface in contact with the resilient membrane to keep the resilient membrane from falling out of the holding flange through the piercing opening.

15. The protective cap according to claim 1, wherein a circumference of the piercing opening at an outer edge of the holding flange is smaller than a circumference of the piercing opening in a plane of the end wall of the membrane holder.

16. The protective cap according to claim 1, wherein said sealing portion of said resilient membrane extending from said inner surface of said end wall is configured for insertion in a circular piercing area of said sealing member of said medical device.

* * * * *

UNITED STATES PATENT AND TRADEMARK OFFICE
CERTIFICATE OF CORRECTION

| | |
|---|---|
| PATENT NO. | : 9,956,138 B2 |
| APPLICATION NO. | : 14/401752 |
| DATED | : May 1, 2018 |
| INVENTOR(S) | : Gunnar Ohlin |

It is certified that error appears in the above-identified patent and that said Letters Patent is hereby corrected as shown below:

On the Title Page

Column 2, Line 2, delete "Gustaysson" and insert -- Gustavsson --

Signed and Sealed this
Thirty-first Day of July, 2018

Andrei Iancu
*Director of the United States Patent and Trademark Office*